United States Patent [19]

Moran et al.

[11] Patent Number: 5,523,017
[45] Date of Patent: Jun. 4, 1996

[54] SOLID CLEANSING BAR

[75] Inventors: Thomas F. Moran, Dublin; Brian O'Briain, Westport; Diarmuid Moran, Dublin, all of Ireland

[73] Assignee: Nephin, Westport, Ireland

[21] Appl. No.: 211,528

[22] PCT Filed: Oct. 7, 1992

[86] PCT No.: PCT/IE92/00013

§ 371 Date: Aug. 8, 1994

§ 102(e) Date: Aug. 8, 1994

[87] PCT Pub. No.: WO93/07245

PCT Pub. Date: Apr. 15, 1993

[30] Foreign Application Priority Data

Oct. 7, 1991 [IE] Ireland .................. 3506/91

[51] Int. Cl.$^6$ .................. C11D 1/88; C11D 3/20
[52] U.S. Cl. ............ 252/174.21; 252/174; 252/DIG. 16; 252/DIG. 2; 252/174.23; 252/542; 252/546
[58] Field of Search .................. 252/174, 174.21, 252/DIG. 16, DIG. 2, 174.23, 542, 546

[56] References Cited

U.S. PATENT DOCUMENTS

| | | | |
|---|---|---|---|
| 2,393,865 | 4/1942 | Wassel | 252/105 |
| 2,806,001 | 9/1957 | Fong et al. | 252/161 |
| 3,903,008 | 9/1975 | Deweever et al. | 252/118 |
| 4,090,973 | 5/1978 | Maguire, Jr. et al. | 252/89 R |
| 4,181,632 | 1/1980 | Schebece | 252/542 |
| 4,545,917 | 10/1985 | Smith et al. | 252/90 |
| 4,554,097 | 11/1985 | Schebece et al. | 252/542 |
| 4,624,713 | 11/1986 | Morganson et al. | 134/25.2 |
| 4,927,557 | 5/1990 | Revis et al. | 252/174.15 |
| 5,064,555 | 11/1991 | Medcalf, Jr. et al. | 252/117 |
| 5,096,608 | 3/1992 | Small et al. | 252/132 |
| 5,342,550 | 8/1994 | Burke et al. | 252/548 |
| 5,433,883 | 7/1995 | Massaro et al. | 252/174.17 |

FOREIGN PATENT DOCUMENTS

| | | |
|---|---|---|
| 738947 | 7/1966 | Canada . |
| 154421 | 9/1985 | European Pat. Off. . |
| 318470 | 5/1989 | European Pat. Off. . |
| 2413561 | 10/1975 | Germany . |
| 4233696 | 4/1994 | Germany . |
| 58507 | 5/1978 | Japan . |
| 78098 | 6/1980 | Japan . |
| 0561774 | 5/1975 | Switzerland . |
| 1543730 | 4/1979 | United Kingdom . |

*Primary Examiner*—Linda Skaling Therkorn
*Assistant Examiner*—Michael P. Tierney
*Attorney, Agent, or Firm*—Jacobson, Price, Holman & Stern

[57] ABSTRACT

A solid cleansing, particularly personal care, especially shampoo, bar comprises from 70% to 80% by weight of a polyethylene glycol (PEG) base system having an average molecular weight between 6,500 and 8,500. The base system may comprise a mixture of PEG 6000, PEG 8000 and PEG 400. The composition includes from 12% to 20% by weight of a detergent which is typically a combination of an anionic surfactant (e.g. a lauryl sulphate) and an amphoteric surfactant (e.g. an imidazoline). Up to 12% of coactive ingredients such as foam stabilizers, pearling agents, emollients and conditioners may also be present.

26 Claims, No Drawings

SOLID CLEANSING BAR

The invention relates to a solid cleansing bar in particular a bar for use as a shampoo bar, a moisturizing bar, a shaving bar and detergent based products generally.

Shampoos and personal care detergent products are generally provided in a liquid form. The shampoos are usually packaged in containers such as plastic bottles or sachets. Leakage can occur due to damage to the containers or failure to replace the lid effectively. Sachets are particularly prone to this leakage difficulty. Further, in use bottles of shampoo are regularly knocked or fall over when opened causing considerable wastage and causing the surfaces of baths and shower trays to become dangerously slippery. Furthermore, when the shampoo is finished, the container is discarded leading to a waste in material resources and adverse environmental effects.

Another disadvantage of liquid shampoo preparations is that it is difficult to control the amount of shampoo applied to a particular area.

Similar comments apply to other similar cleansing compositions.

This invention is directed towards providing an approved cleansing bar which will overcome at least some of these difficulties.

CH-A-561 774 describes an iodine-containing pharmaceutical cleansing germicidal bar comprising polyoxyethylene glycols with a molecular weight of from 1,540 to 6,000, a primary alkanol, a detergent and an iodophor.

Patent Abstracts of Japan Vol 11, No. 139 (C-420) 1986 and JP-A-61277608 describes a perfumed solid product for showering including polyethylene glycol having an average molecular weight of from 1,000 to 6,000.

According to the invention there is provided a solid cleansing bar comprising a detergent; and at least 65% of weight of a polyethylene glycol base system having an average molecular weight of between 6,500 and 8,500.

In a preferred embodiment of the invention the composition has a melting point of greater than 40° C.

In a preferred embodiment of the invention the polyethylene glycol base system is present in an amount of between 65% and 85% by weight, most preferably between 70% and 80% by weight.

In one arrangement the polyethylene glycol base system comprises at least two polyethylene glycols of different molecular weights. Typically one polyethylene glycol has a molecular weight of approximately 8,000.

In one arrangement the polyethylene glycol having a molecular weight of approximately 6,000 is present in an amount of from 30% to 45% by weight of composition.

In one embodiment of the invention, the polyethylene glycol base system includes a softening polyethylene glycol having a molecular weight of between 100 and 800.

Preferably the softening polyethylene glycol has a molecular weight of 400. Most preferably the composition includes from 1% to 8%, most preferably from 3% to 7% by weight of the softening polyethylene glycol.

In a particularly preferred embodiment to the invention, the pH of a 1% solution of the composition in water is from 5.5 to 8.0, most preferably between 6.0 and 7.0.

In an especially preferred embodiment to the invention, the melting point of the cleansing bar is from 43° C. to 46° C.

In a particularly preferred embodiment of the invention the detergent comprises from 8% to 30% by weight of the composition. Most preferably the detergent comprises from 12% to 20% by weight of the composition.

In one arrangement the detergent includes an anionic surfactant.

In another arrangement the detergent includes an amphoteric surfactant.

In an especially preferred embodiment of the invention the detergent is formed by a detergent system comprising at least two detergents.

The anionic surfactant may preferably comprise a lauryl sulfate.

The amphoteric surfactant may preferably comprise an imidazoline.

In one particularly preferred arrangement the detergent comprises a mixture of a lauryl sulfate and an imidazoline.

In a particularly preferred embodiment the invention the composition includes up to 12% by weight of coactive ingredients. These may be selected from one or more of foam stabilizers, pearling agents, emollients, thickeners, wetting agents, superfatting agents, water binders, waxes, skin tonics and lotions, conditioners, softeners, proteins, secondary detergents and cleansing agents.

In a preferred arrangement the coactive ingredients are present in an amount of from 1% to 8% by weight of the composition.

In one embodiment of the invention the cleansing bar includes a betaine such as lauryl dimethyl betaine.

In another embodiment of the invention the cleansing bar includes a foam stabilizer such as coconut diethanolamide.

In a further embodiment of the invention the cleansing bar compositions includes a conditioner such as protein collagen.

In an especially preferred embodiment of the invention the cleansing bar is a shampoo bar.

In another embodiment of the invention the cleansing bar is a shaving bar.

In a further embodiment to the invention the cleansing bar is a moisturizing bar.

The cleansing bar may also comprise a skin cleansing bar or a conditioning bar.

The invention will be more clearly understood from the following description thereof given by way of example only.

In the examples the quantities of the ingredients used are given in percentage by weight of the final composition. In each case the cleansing bar composition is preferably prepared by melting the polyethylene glycol base system adding the main detergent to the melted polyethylene glycol base system, and, subsequently adding the remaining ingredients to the system during mixing. The formulation thus formed is then poured into a mold at a temperature of between 60° and 68° C. and is removed from the mould after setting to provide a cleansing bar of desired size and shape. Alternatively the mould may define a container for the cleansing bar for subsequent packaging.

In each case a solid cleansing bar is formed having a melting point of between 40° and 50° C. and a pH in a 1% solution in water of between 6.0 and 7.0.

EXAMPLE 1

Antidandruff Shampoo Bar 1

| | |
|---|---|
| Polyethylene glycol 6000 | 40% |
| Polyethylene glycol 8000 | 35% |
| Ammonium alkyl ether sulfate | 15% |
| Coconut imidazoline | 6% |

EXAMPLE 2

Antidandruff Shampoo Bar 2

| | |
|---|---|
| Cocoamidopropyl betaine | 2.5% |
| Selenium disulhide (2.5%) | 1% |
| Fragrance | 0.5% |

| | |
|---|---|
| Polyethylene glycol 6000 | 39% |
| Polyethylene glycol 8000 | 35% |
| Sodium $C_{14-16}$ olefin sulfonate | 13% |
| Coconut imidazoline | 6% |
| Lauryl dimethyl betaine | 3% |
| Sodium N-lauryl sarcosinate | 3.5% |
| Octopirox | 0.5% |
| Fragrance | 0.5% |

EXAMPLE 3

Mild Shampoo Bar 1

| | |
|---|---|
| Polyethylene glycol 6000 | 35% |
| Polyethylene glycol 8000 | 36% |
| Lauryl ether sulphates;<br>(Sodium & magnesium lauryl ether sulfates) | 13% |
| Coconut imidazoline | 6% |
| Polyethylene glycol 400 | 4% |
| Myristyl dimethyl amine oxide | 3% |
| Sucrose monococoate | 2% |
| Fragrance | 1% |

EXAMPLE 4

Conditioner Shampoo Bar

| | |
|---|---|
| Polyethylene glycol 6000 | 40% |
| Polyethylene glycol 8000 | 30% |
| Lauryl ether sulfates;<br>(Sodium & magnesium lauryl ether/sulfates) | 15% |
| Sodium N-methyl cocoyl taurate | 4.5% |
| Lauryl dimethyl betaine | 4% |
| Coconut diethanolamide | 3% |
| Quaternised hydrolysed collagen | 3% |
| Preservative | 0.2% |
| Fragrance | qs |

EXAMPLE 5

Shaving Bar (Suitable for Use with a Shaving Brush)

| | |
|---|---|
| Polyethylene glycol 6000 | 40% |
| Polyethylene glycol 8000 | 33% |
| Glycerol monosterate | 7% |
| Cetyl stearyl alcohol | 5% |
| Glycerol | 5% |
| Polyethylene glycol 400 | 4% |
| Liquid parafin | 3% |
| Cocoamidopropyl betaine | 2.5% |
| Chlorobenzyl alcohol | 0.2% |
| Fragrance | qs |

EXAMPLE 6

A Shaving Bar (Brushless)

| | |
|---|---|
| Polyethylene glycol 6000 | 41% |
| Polyethylene glycol 8000 | 36% |
| Sodium lauryl ether sulfate | 10% |
| Lauryl Dimethyl Betaine | 6% |
| Coconut diethanolamide | 4% |
| Mineral oil | 2% |
| Silicone fluid | 0.4% |
| Preservative | 0.2% |
| Fragrance | 0.4% |

EXAMPLE 7

Moisturizing Bar

| | |
|---|---|
| Polyethylene glycol 6000 | 40% |
| Polyethylene glycol 8000 | 34% |
| Liquid parafin & lanolin alcohol | 7% |
| Cetyl acetate & acetylate lanolin alcohol | 5% |
| Glycerol monostearate | 4% |
| Stearic acid | 3% |
| Liquid parafin | 3% |
| Propylene glycol | 2% |
| Herbal & natural extracts | 2% |

EXAMPLE 8

Shampoo Bar

| | |
|---|---|
| Polyethylene glycol 6000 | 33.2% |
| Polyethylene glycol 8000 | 33.2% |
| Sodium lauryl ether sulfate | 26.6% |
| Ethoxilated fatty alcohol | 2.0% |
| Quaternized hydrolyzed collagen | 1.3% |
| Lauryl dimethyl betaine | 2.7% |
| Dioctyl succinate | 0.4% |
| Fragrance | 0.4% |

The product of example 8 is prepared by mixing the polyethylene glycols and heating to 70° C. The sodium lauryl ether sulfate and the ethoxylated fatty alcohol are then added and mixing is continued. Quaternized hydrolyzed collagen, lauryl dimethyl betaine, dioctyl succinate and preservative are then added, mixing is continued and the fragrance is added at 60° C. The composition is poured into a mold when mixture is in the 60° to 68° C. temperature range. When the mixture has hardened the solid cleansing bar thus formed is removed from mold.

EXAMPLE 9

Skin Cleansing Bar

| | |
|---|---|
| Polyethylene glycol 10,000 | 15.0% |
| Polyethylene glycol 8,000 | 20.0% |
| Polyethylene glycol 6,000 | 40.0% |
| Light mineral oil | 12.0% |
| Sucrose Tripalmitic acid | 7.0% |
| Glycerol | 5.5% |
| Fragrance and Preservative | 0.5% |

The above examples illustrate formulations and methods for the production of a solid bar for personal use.

The characteristics of the polyethylene glycol base system matrix that are necessary for incorporation in effective solid cleansing products according to the invention include the following:

(a) The base system is solid with good solubility characteristics in warm water (b) Non-ionic and not sensitive to electrolytes that may be present for example in hard water.

(c) Flexibility in design of tactile properties of bars for different applications. This is typically achieved by mixing different grades of polyethylene glycols.

(d) The system is non volatile and thermally stable and of low reactivity. Consequently the system is stable and not reactive to many substances such as detergents and packaging materials.

(e) The system is physiologically safe as it is non-toxic. It is also non-irritant and non-sensitizing. This is particularly the case because the pH is close to that of the skin.

(f) The system is ecologically safe and acceptable because it is biodegradable (over time) and is non-toxic to plant or animal life such as fish and bacteria.

(g) The system has excellent miscibility properties with a wide range of substances (including detergents) and forms homogenous mixtures when molten or in solid form.

(h) The system is mouldable when heated allowing any desired shape to be formed.

(i) The system is capable of holding up to 35% of other ingredients such as detergent(s).

PEG 400—or a similar molecular weight PEG or PEG derivative, may be inclined to counteract excessive drying of the product.

The melting point must be greater than 40° C. and preferably approximately 43° C. to 46° C.

The pH for a 1% solution of the composition in water is preferably between 5.5 to 8, most preferably around 6.2. (In contrast, soap can be pH 9 and natural skin's pH is approximately 5.5).

The second essential feature of the product is (are) the (main) detergent(s). This is the primary active system. The main detergent is most often an anionic surfactant although amphoterics can also fulfill this role.

Thus the "base detergent" is in most cases anionic and this will represent between 8% and 30% W/W of the product. Blends of the basic detergents can also be used. Frequently used are the imidazoline with lauryl sulfates (amphoterics+anionics).

The most preferred basic detergents are listed in order below:

Lauryl sulfates; TEA-, sodium-, ammonium-, magnesium
Lauryl ether sulphates; sodium lauryl ether sulphate
Fatty alcohol sulphates;
Fatty alcohol ether sulphates; ammonium alkyl ether sulphate
Sulfonates; Sodium $C_{14-18}$ olefin sulphonate
Phosphates
Mono alkyl sulfosuccinates; disodium lauric monoethanolamide sulfosuccinate disodium lauric ethoxy sulfosuccinate disodium undecylinic monoethanolamide sulfosuccinate disodium cocomonoethanolamide ethoxy sulphosuccinate disodium alkyl ethoxy sulfosuccinate disodium lauryl (or alkyl) sulfosuccinate
Alkyl imidazoline; coconut imidazoline These basic detergents are usually supplemented by coactive ingredients which include components which combine with the "basic detergent" and/or other coactive ingredients to positively contribute to the overall product performance.

The coactive ingredients act, for example, as foam stabilizers, pearling agents, emollients, thickeners, wetting agents, superfatting agents, water binders, waxes, skin tonics & lotions, conditioners, softeners, proteins and secondary detergents & cleaning agents.

The combinations of coactive ingredients and "basic detergents" contribute to the performance of the final products due to synergistic polar, solubility and foaming related interactions.

Important coactive ingredients include those listed below but also include some of the basic detergents if found in lower concentrations. The W/W concentrations of these coactive agents is between 1% and 8% in general, although up to 12% of these coactive ingredients can be present particularly where the "basic detergent's" concentration is below 16%. These ingredients include surfactants (all types) and other recognized personal care ingredients.

List of Coactive Ingredients

Sarcosinates
  (sodium N-lauroyl sarcosinate)
  (TEA lauroyl sarcosinate)
  (lauroyl sarcosine)
Quaternized dihydroimidazole
Sodium N-methyl-N oleoyl taurates
Sodium N-methyl-N cocoyl taurates
Glycerol
Propylene glycol
Acyl N-methyl taurides
Fatty esters of isethionic acid
Liquid parafin
Alkyl sulfoacetate
Acyl glutamate
Lanolin & lanolin derivatives cholesterol, lanolin, lanolin alcohols
Hydrophilic oils: PEG-7-glyceryl cocoate
Emollient esters: isostearyl neopentanoate, lauryl lactate,
Fatty acid alkyolamides (mono & diamides: lauric isopropanolamide (& monoethanolamide); coconut (& lauric) diethanolamide
Fatty acid esters: glycerol monostearate, ethylene glycol monostearate
Mild teritary amino salts
Proteins & hydrolyzed collagens, amino acids, keratins, etc
Tertiary amine derivatives:
  lauryl dimethyl betaine,
  lauryl (or myristyl dimethyl amine
  oxide
Amphoteric surfactants: cocoamidopropyl betaine
Nonionic surfactants: sucrose monococoate
Phosphate esters of fatty alcohol ethoxylates
Stearic acid In addition to the coactive ingredients colors, fragrances, medicaments, antibacterial, astringents, deodorant, exfoliating and antidandruff substances may be added in concentrations generally between 0.5% and 5%. Some of these substances are listed below:

Octopirox (0.5%–0.8%)
Coal tar extracts (1%–5%)
Herbal & natural extracts
Sulfur powder
Citric acid
Zinc omadine (1%–2%)
Selenium disulfide Zinc piridine thiol oxide
Abrasives (almond & olive shell granules) (5%–15%)
Dichlorobenzyl alcohols (0.2%–0.5%)

Advantageously, the cleansing bar according to the present invention overcomes the leakage problems associated with shampoos which are typically provided in liquid form. Furthermore, the cleansing bar can be packaged in a biodegradable wrapper which overcomes the environmental difficulties with plastic containers and is also cheaper and less wasteful than the plastic containers. Obviously also there is no spillage problem with a solid cleansing bar and this adds to the portability of the product.

Advantageously, the detergent included in the cleansing bar may be such that the bar can be used as a combined soap/shampoo bar. This would be particularly advantageous in many situations for example for travel convenience or in the hotel industry where a single cleansing bar could be provided rather than the currently used separate soap bar and shampoo sachet or container. The combined shampoo/soap bar would be less wasteful and cheaper to produce.

Another advantage of the bar cleansers over liquid preparations is that particular areas can be more easily targeted for higher application rates. An example of this is combination skin where some patches of skin or locations on the scalp can be more oily or drier than normal and these receive more or less application as necessary.

The cleansing bar can advantageously be molded to any desired shape or configuration, and coloring agents may also be added to the ingredients, if desired.

It is envisaged that the exemplary ingredients listed above for the cleansing bar may be added to, or changed with the exception of the polyethylene glycol and detergent.

As will be apparent from example 10 below it is envisaged that solid cleansing bars including detergents for clothes washing and dishwashing supported by a polyethylene glycol carrier may be provided. Typically, a pre-set measured amount of detergent would be contained in each bar, the amount being typically a unit amount required for a particular cleaning operation. Thus, a cleansing bar with the required amount of detergent to clean a single load of clothes in a clothes washer, or for cleaning a load of dishes in a dish washer for example, may be provided.

EXAMPLE 10

Solid Dishwashing Detergent

| Polyethylene glycol 8,000 | 54% |
|---|---|
| Detergent | 20% |
| Fatty acid dialkylolamide | 3% |
| Ammonium non-oxynol-4-sulfate | 19% |
| Sodium xylene sulfonate | 4% |

Heat the polyethylene glycol 8000 to 75° C. and incorporate the other ingredients individually blending each fully. Allow to cool and pour into mould at approximately 60° C.

The invention is not limited to the embodiments hereinbefore described which may be varied in detail.

We claim:

1. A solid cleansing bar composition consisting essentially of:
   (A) a detersive effective amount of at least one surfactant selected from the group consisting essentially of anionic surfactants, nonionic surfactants and mixtures thereof with an additional surfactant which is an amphoteric surfactant which is present in an amount of from about 2 to about 9% by weight of the cleaning bar; and
   (B) polyethylene glycol having an average molecular weight range of from 6500 to 8500 present in an amount of at least 65% by weight of the cleansing bar.

2. A cleansing bar composition as claimed in claim 1 wherein the composition has a melting point of greater than 40° C.

3. A cleansing bar composition as claimed in claim 1 wherein the polyethylene glycol base system is present in an amount of between 65% and 85% by weight.

4. A cleansing bar composition as claimed in claim 1 wherein the polyethylene glycol base system is present in an amount of between 70% and 80% by weight.

5. A cleansing bar composition as claimed in claim 1 wherein the polyethylene glycol base system comprises at least two grades of polyethylene glycols of different molecular weights.

6. A cleansing bar composition as claimed in claim 1 wherein one polyethylene glycol has a molecular weight of approximately 6,000 and another polyethylene glycol has a molecular weight of approximately 8,000.

7. A cleansing bar composition as claimed in claim 6 wherein the polyethylene glycol having a molecular weight of approximately 6,000 is present in an amount of between 30% to 45%, by weight of the composition.

8. A cleansing bar composition as claimed in claim 1 wherein the polyethylene glycol base system includes a softening polyethylene glycol having a molecular weight of between 100 and 800.

9. A cleansing bar composition as claimed in claim 8 wherein the softening polyethylene glycol has a molecular weight of 400.

10. A cleansing bar as claimed in claim 8 wherein the composition includes from 1% to 8% by weight of the softening polyethylene glycol.

11. A cleansing bar composition as claimed in claim 8 wherein the composition includes from 3% to 7% by weight of the softening polyethylene glycol.

12. A cleansing bar composition as claimed in claim 1 wherein the pH of a 1% solution of the composition in water is from 5.5 to 8.0.

13. A cleansing bar composition as claimed in claim 12 when the pH is approximately 6.0 to 7.0.

14. A cleansing bar composition as claimed in claim 1 wherein the melting point of the composition is approximately 43° C. to 46° C.

15. A cleansing bar composition as claimed in claim 1 wherein the detergent comprises from 8% to 30% by weight of the composition.

16. A cleansing bar composition as claimed in claim 15 wherein the detergent comprises from 12% to 20% by weight of the composition.

17. A cleansing bar composition as claimed in claim 1 wherein the detergent includes an anionic surfactant.

18. A cleansing bar composition as claimed in claim 17 wherein the anionic surfactant comprises a lauryl sulphate.

19. A cleansing bar composition as claimed in claim 1 wherein the amphoteric surfactant comprises an imidazoline.

20. A cleansing bar composition as claimed in claim 1 wherein the detergent comprises a lauryl sulfate and an imidazoline.

21. A cleansing bar composition as claimed in claim 1 wherein the cleansing bar includes a betaine.

22. A cleansing bar composition as claimed in claim 1 wherein the betaine comprises lauryl dimethyl betaine.

23. A cleansing bar composition as claimed in claim 1 including a foam stabilizer.

24. A cleansing bar composition as claimed in claim 23 wherein the foam stabiliser comprises coconut diethanolamide.

25. A cleansing bar composition as claimed in claim 1 including a conditioner.

26. A cleansing bar composition as claimed in claim 25 wherein the conditioner comprises protein collagen.

* * * * *